United States Patent [19]

Irie et al.

[11] Patent Number: 4,786,737
[45] Date of Patent: * Nov. 22, 1988

[54] AROMATIC SULFONIC ACID SALTS OF A PROLINE DERIVATIVE

[75] Inventors: Yasuo Irie; Fusayoshi Kakizaki; Chieko Ishijima; Michito Sumikawa; Naohiko Yasuda, all of Kawasaki, Japan

[73] Assignee: Ajinomoto Co., Inc., Tokyo, Japan

[*] Notice: The portion of the term of this patent subsequent to Jan. 19, 2005 has been disclaimed.

[21] Appl. No.: 93,240

[22] Filed: Sep. 4, 1987

Related U.S. Application Data

[63] Continuation of Ser. No. 934,563, Nov. 25, 1986, Pat. No. 4,720,554.

[30] Foreign Application Priority Data

Dec. 6, 1985 [JP] Japan ................... 60-274678

[51] Int. Cl.⁴ .......................................... C07D 207/09
[52] U.S. Cl. .................................................... 548/533
[58] Field of Search ......................................... 548/533

[56] References Cited

U.S. PATENT DOCUMENTS 4,374,829 2/1983 Harris et al. ............... 260/112.5 R
4,720,554 1/1988 Irie et al. ............................ 548/533

OTHER PUBLICATIONS

Review of Biochemistry, 1969, pp. 24, 28, 29, the Macmillan Co., Collier-Macmillan Ltd., London.
Pettit, Synthetic Peptides, vol. 5, Elsenier Scientific Publishing Co., N.Y. (1980), [pages unknown].
C.A., 106: 19027t, Blacklock et al. (1987).
C.A., 68: 30033j, Anfinsen et al. (1968).
C.A., 105: 60951g, Blacklock et al. (1986).

Primary Examiner—Joseph P. Brust
Attorney, Agent, or Firm—Oblon, Fisher, Spivak, McClelland & Maier

[57] ABSTRACT

A compound which is:

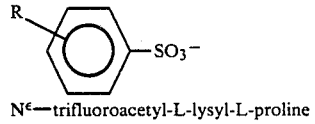

N$^\epsilon$—trifluoroacetyl-L-lysyl-L-proline wherein R may be 1 to 5 H, Cl, Br, F, $C_1$-$C_4$ straight chain or branched alkyl, OH, or $CF_3$.

5 Claims, No Drawings

AROMATIC SULFONIC ACID SALTS OF A PROLINE DERIVATIVE

This is a continuation of application Ser. No. 06/934,563, filed Nov. 25, 1986, issued Jan. 19, 1988, as U.S. Pat. No. 4,720,554.

BACKGROUND OF THE INVENTION

1. Field of the Invention

The invention relates to $N^\epsilon$-trifluoroacetyl-lysyl-proline aromatic sulfonic acid salts.

2. Description of the Related Art

The synthetic intermediate peptide lysyl-proline and its derivatives are useful in preparing important products such as Tuftsin which possesses an immunity-increasing action (Tuftsin: L-threonyl-L-lysyl-L-prolyl-L-arginine, Ann. N.Y. Acad. Sci., vol. 419, 12, 1983) and Lisinopril which possesses a blood pressure-lowering action (Lisinopril: N-α-(1(S)-carboxy-3-phenylpropyl)-L-lysyl-L-proline, Japanese first patent publication No. 81845/1980), and others. Synthetic procedures for producing such compounds are often based on the important dipeptide derivative $N^\epsilon$-trifluoroacetyl-L-lysyl-L-proline as a starting material. This starting material has been found to be unstable and is easily converted into a diketopiperazine (II) as shown in the following equation:

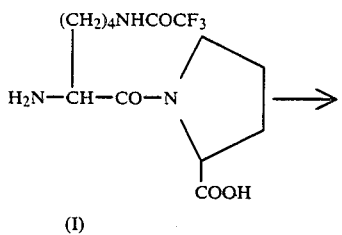

(I)

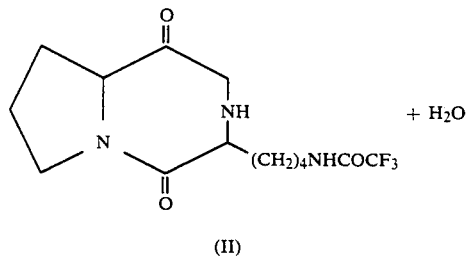

(II)

There is no known stable and easily handled form of $N^\epsilon$-trifluoroacetyl-L-lysyl-L-proline. In view of the importance of this dipeptide derivative as a starting material, and the fact that known forms of this starting material are unstable and hard to manage, there remains a great need for new and more stable forms of this starting material. In particular, there is a need for a stable crystal of $N^\epsilon$-trifluoroacetyl-L-lysyl-L-proline in the free form or in stable salt form.

SUMMARY OF THE INVENTION

Accordingly, it is an object of the present invention to provide stable crystals of $N^\epsilon$-trifluoroacetyl-L-lysyl-L-proline salts.

This and other objects have been surprisingly satisfied by the discovery that aromatic sulfonic acid salts of $N^\epsilon$-trifluoroacetyl-L-lysyl-L-proline are easily handled and possess high stability.

DESCRIPTION OF THE PREFERRED EMBODIMENTS

The present inventors tried to crystallize $N^\epsilon$-trifluoroacetyl-L-lysyl-L-proline in free form using dozens of different kinds of solvents in an attempt to produce a stable manageable crystal of this dipeptide derivative. However, in none of these cases was such a stable crystal obtained. In fact, the compound was quite difficult to crystallize at all.

The present inventors then prepared many freeze dried salts between the peptide in the free form and several different kinds of acids, and tested them for the ease in handling and stability thereof. As a result of such testing, the inventors surprisingly found that aromatic sulfonic acid salts of the dipeptide derivative were outstandingly easy to handle and simultaneously possessed high stability.

By "free form" is meant that the peptide derivative is not involved in salt form with an acid, although internal salt formation may be present.

By aromatic sulfonic acid salt according to the present invention, is meant a salt form of the peptide derivative derived from acids having the following structure:

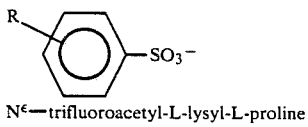

$N^\epsilon$—trifluoroacetyl-L-lysyl-L-proline wherein R may be 1 to 5 of H, Cl, Br, F, $C_1$–$C_4$ straight chain or branched alkyl, OH, or $CF_3$. R is preferably 1 of the above-named substituents and is preferably in the para position relative to the sulfonic acid group. Some specific examples of aromatic sulfonic acids which may be used in salt form are benzenesulfonic acid, p-toluenesulfonic acid, p-bromobenzenesulfonic acid, p-hydroxybenzenesulfonic acid, xylenesulfonic acid, and cumenesulfonic acid. Of these, p-toluenesulfonic acid and benzenesulfonic acid are preferred.

The peptide portion of the molecule is preferably $N^\epsilon$-trifluoroacetyl-L-lysyl-L-proline. However, derivatives thereof wherein a hydrogen is substituted by a halogen such as Cl, Br or F; as well as D isomers of lysine or proline are also possible. Other $N^\epsilon$ acyl moieties such as acetyl are also possible.

In the following table, stability test results for several different kinds of freeze-dried products which were prepared are shown. The ratio of diketopiperazine production was obtained by high performance liquid chromatography (HPLC) measurements.

TABLE 1

| | | | Result of Stability Test | | | | |
|---|---|---|---|---|---|---|---|
| Sample No. | Sample | Preserving Temperature | Number of days elapsed and Ratio of producing diketopiperazine (%) | | | | |
| | | | 0 day | 5 | 10 | 20 | 30 |
| 1 | Free form | 5° C. | 0% | 0.2 | 0.6 | 0.8 | 1.1 |
| 2 | Free form | 30 | 0 | 2.5 | 3.3 | 5.2 | 11.6 |
| 3 | Hydrochloric acid salt | 5 | 0 | 0 | 0 | 0 | 0 |
| 4 | Hydrochloric acid salt | 30 | 0 | 0 | 0 | 0 | 0 |
| 5 | p-Toluenesulfonic acid salt | 5 | 0 | 0 | 0 | 0 | 0 |
| 6 | p-Toluene- | 30 | 0 | 0 | 0 | 0 | 0 |

TABLE 1-continued

| | | Result of Stability Test | | | | |
|---|---|---|---|---|---|---|
| Sample No. | Sample | Preserving Temperature | \multicolumn{5}{c}{Number of days elapsed and Ratio of producing diketopiperazine (%)} |
| | | | 0 day | 5 | 10 | 20 | 30 |
| | sulfonic acid salt | | | | | | |
| 7 | Benzenesulfonic acid salt | 30 | 0 | 0 | 0 | 0 | 0 |
| 8 | Tartaric acid salt | 30 | 0 | 1.3 | 2.5 | 4.2 | 6.8 |
| 9 | Malic acid salt | 30 | 0 | 3.3 | 6.0 | 10.6 | 17.5 |
| 10 | Citric acid salt | 30 | 0 | 0.8 | 2.2 | 4.4 | 6.5 |

It is evident from the above table that in the case of the free form of the dipeptide derivative and the carboxylic acid salts, the amount of diketopiperazine (II) production increased as the days passed. On the other hand, no diketopiperazine (II) is produced at all in the case of the hydrochloric acid salt, the p-toluenesulfonic acid salt and the benzenesulfonic acid salt. Although the hydrochloric acid salt was stable, this material was not easily managed. This is because the hydrochloric acid salt is candy-like, and highly deliquescent. Accordingly, the hydrochloric acid salt is very difficult to weigh out so errors in weighing are hard to avoid. On the other hand, the p-toluenesulfonic acid salt and the benzenesulfonic acid salts are powder-like, do not deliquesce, and are quite easy to handle and weigh out. Thus, these compounds can be easily stored and used for synthesis.

The aromatic sulfonic acid salts of the present invention can be obtained, for example, by adding the aromatic sulfonic acids such as p-toluenesulfonic acid to an aqueous solution of $N^\epsilon$-trifluoroacetyl-L-lysyl-L-proline in a ratio of 1 mole of the sulfonic acid to 1 mole of the peptide, thereby making a homogeneous solution, and freeze drying the product. $N^\epsilon$-trifluoroacetyl-L-lysyl-L-proline may be obtained by well-known methods of peptide synthesis.

The $N^\epsilon$-trifluoroacetyl-L-lysyl-L-proline aromatic sulfonic acid salts of the present invention may be used to synthesize known peptide products such as tuftsin and lisinopril, and derivatives thereof. For example, compounds of the following structure may be synthesized:

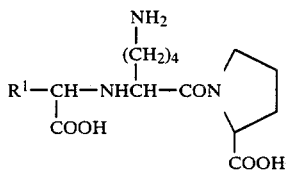

wherein $R^1$ represents a $C_1$–$C_4$ alkyl group, an aralkyl group such as benzyl, 2-phenylethyl, 3-phenylpropyl, or an aryl group such as phenyl and naphthyl. The synthetic method comprises converting $N^\epsilon$-trifluoroacetyl-L-lysyl-L-proline aromatic sulfonic acid salt to the free form thereof by neutralization with an alkaline solution of, for example, sodium carbonate, sodium bicarbonate, triethylamine, dilute sodium hydroxide, etc., reacting the free $N^\epsilon$-trifluoroacetyl-L-lysyl-L-proline with an α-keto acid ester having the structure $$R^1-CO-COOR^2$$

to produce an $N^\epsilon$-trifluoroacetyl-L-lysyl-L-proline derivative having the following structure

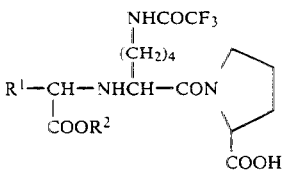

wherein $R^1$ is as defined above and $R^2$ stands for hydrogen, or a $C_1$–$C_4$ alkyl group, and hydrolyzing the trifluoroacetyl protecting group.

Solvents, reaction times, the means of removing the trifluoroacetyl group, and the reaction conditions for coupling the α-keto acid ester with the peptide derivative are illustrated in the examples herein below.

The invention now being generally described, the same will be better understood by reference to certain specific examples which are included herein for purposes of illustration only and are not intended to be limiting of the invention or any embodiment thereof, unless specified.

EXAMPLES

EXAMPLE 1

$N^\epsilon$-Benzyloxycarbonyl-$N^\epsilon$-trifluoroacetyl-L-lysyl-L-proline benzyl ester (135 g) was dissolved in a mixture of methanol (650 ml) and water (200 ml), and 2% palladium-carbon catalyst (50 g) involving 56% of water was added thereto. A reduction reaction was carried out by bubbling hydrogen gas into the solution for 3 hours at room temperature. After completion of the reaction, the catalyst was removed by filtration. The thus obtained filtrate was concentrated under reduced pressure to distill off methanol.

The quantity of $N^\epsilon$-trifluoroacetyl-L-lysyl-L-proline obtained was determined by high performance liquid chromatography (HPLC). After that, an equimolar amount of p-toluenesulfonic acid monohydrate (44.7 g) was added to the concentrated solution to make a homogeneous solution. The solution was freeze-dried to give $N^\epsilon$-trifluoroacetyl-L-lysyl-L-proline p-toluenesulfonic acid salt yielding 120 g (97.1%).

Content of water: 0.7%

Specific rotation: $[\alpha]_D^{20} -32.1°$ (C=2, H$_2$O)

No diketopiperazine was contained therein as determined by high performance liquid chromatography.

Next, a reaction and treatment of the above mentioned example 1 without addition of p-toluenesulfonic acid monohydrate was carried out to give $N^\epsilon$-trifluoroacetyl-L-lysyl-L-proline in the free form yielding 77.5 g (92.3%).

Content of water: 0.9%

Specific rotation: $[\alpha]_D^{20} -4.82°$ (C=2, H$_2$O)

2.3% by weight of diketopiperazine was contained therein as measured by high performance liquid chromatography.

EXAMPLE 2

Example 1 wherein p-toluenesulfonic acid mono hydrate (44.7 g) was replaced by benzenesulfonic acid (36.7 g) was repeated to obtain Nc-trifluoroacetyl-L-lysyl-L-proline benzenesulfonic acid salt yielding 115 g (95.4%).

Content of water: 1.0%
Specific rotation: $[\alpha]_D^{20} -32.7°$ (C=2, H$_2$O)
There was no diketopiperazine therein as determined by high performance liquid chromatography.

COMPARATIVE EXAMPLE

Production of N$^\epsilon$-(1-(S)-carboxy-3-phenylpropyl)-L-lysyl-L-proline

N$^\epsilon$-Trifluoroacetyl-L-lysyl-L-proline p-toluenesulfonic acid salt (50.1 g), 2-oxo-4-phenylbutyric acid ethyl ester (30.9 g), triethylamine (10.1 g), molecular sieves 3A produced by Junsei Chemical Co. (100 g) and Raney nickel (30 g) were added to ethanol (1 l), and the mixture was stirred at 25° C. with hydrogen (3 kg/cm2) to effect hydrogenation. After completion of hydrogen absorption, the solution was filtered and the obtained solid substance was washed with ethanol (300 ml). The filtrate was mixed with the ethanol wash solution, and then the solution was concentrated. Water (300 ml) and methylene chloride (300 ml) were added to the above concentrated solution. The pH was adjusted to 9.2 with an aqueous sodium hydroxide solution to make two phases. The water solution was obtained by separation, and then washed with methylene chloride (300 ml) two times. Next, the water solution was adjusted to pH 4.6 with hydrochloric acid, and then extracted with methylene chloride (300 ml). The methylene chloride solution was dried over anhydrous sodium sulfate, and concentrated. To the concentrated solution methyl t-butyl ether (300 ml) was added and the solution was warmed to make a homogeneous solution. The solution was cooled under stirring to precipitate a crystal, and cyclohexane (110 ml) was added thereto. The mixture was stirred for 2 hours. Next, the mixture was filtered and the thus obtained crystals were dried under reduced pressure to obtain N$^\epsilon$-(1-(S)-ethoxycarbonyl-3-phenylpropyl)-N$^\epsilon$-trifluoroacetyl-L-lysyl-L-proline yielding 26.1 g.

10% aqueous sodium hydroxide solution (150 ml) was added to the above product, and the solution was stirred at 25° C. for 3 hours. This solution was passed through a strongly acidic ion exchanging resin (Diaion SK-1B, H+ type produced by Mitsubishi Chemical Industries) and then washed with water. The solution was extracted with 4% aqueous pyridine solution. The eluted solutions were mixed and then concentrated to 250 ml. The solution was adjusted to pH 5.2 with hydrochloric acid, and concentrated to 57 grams. Ethanol (300 ml) was added thereto to make a homogeneous solution. The solution was cooled to precipitate crystals and the crystals were isolated by filtration, and dried to obtain N$^\epsilon$-(1-(S)carboxy-3-phenylpropyl)-L-lysyl-L-proline 2H$_2$O yielding 20.2 g.

Content of water: 8.3% by the Karl Fischer method
Specific rotation: $[\alpha]_D^{25} -26.6°$ (C=2, 0.1N HCl-methanol).

The invention now being fully described, it will be apparent to one of ordinary skill in the art that many changes and modifications can be made thereto without departing from the spirit or scope of the invention as set forth herein.

What is claimed as new and desired to be secured by Letters Patent of the United States is:

1. A method of producing a lysylproline derivative represented by the following formula:

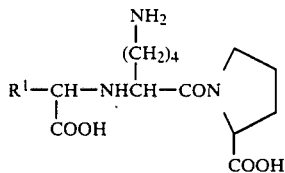

which comprises, converting to free form by neutralization with an alkaline solution, an N$^\epsilon$-trifluoroacetyl-L-lysyl-L-proline aromatic sulfonic acid salt having the formula:

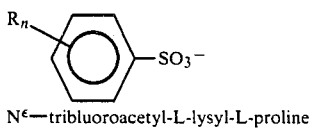

N$^\epsilon$—tribluoroacetyl-L-lysyl-L-proline wherein n is 0 to 5, R is Cl, Br, F, C$_1$-C$_4$ straight chain or branched alkyl, OH, or CF$_3$;

reacting the neutralized salt with an $\alpha$-keto ester having the formula

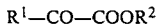

wherein said reaction is conducted in the presence of hydrogen or a reducing agent, to produce an N$^\epsilon$-trifluoroacetyl-L-lysyl-L-proline derivative having the following formula:

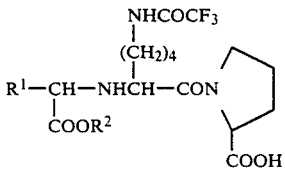

and hydrolyzing the trifluoroacetyl protecting group from said derivative, wherein R$^1$ is selected from the group consisting of C$_1$-C$_4$ alkyl groups, benzyl, 2-phenylethyl, 3-phenylpropyl, phenyl, and naphthyl, and R$^2$ is selected from the group consisting of hydrogen and C$_1$-C$_4$ alkyl groups.

2. The process according to claim 1, wherein said neutralization is effected by treatment with sodium carbonate, sodium bicarbonate, triethylamine, or diisopropylethylamine.

3. The process according to claim 1, wherein said hydrolysis is effected by treatment with sodium hydroxide.

4. The process according to claim 1, wherein said $\alpha$-keto acid ester is reacted with said derivative under reducing conditions.

5. The process according to claim 1, wherein said reducing agent is sodium cyanoborohydride.

* * * * *

UNITED STATES PATENT AND TRADEMARK OFFICE
CERTIFICATE OF CORRECTION

PATENT NO. : 4,786,737
DATED : NOVEMBER 22, 1988
INVENTOR(S) : YASUO IRIE ET AL

It is certified that error appears in the above-identified patent and that said Letters Patent is hereby corrected as shown below:

Column 4, line 30, change "Nε-Benzyloxycarbonyl" to --Nα-Benzyloxycarbonyl--.

Column 4, line 66, change "Nc-trifluoroacetyl" to --Nε-trifluoroacetyl--.

Column 5, line 8, change "Nε-(1-(S)-carboxy" to --Nα-(1-(S)-carboxy--.

Column 5, line 38, change "Nε-(1-(S)-ethoxycarbonyl" to --Nα-(1-(S)-ethoxycarbonyl--.

Column 5, line 54, change "Nε-(1-(S)carboxy" to --Nα-(1-(S)carboxy--.

Signed and Sealed this

Nineteenth Day of December, 1989

Attest:

JEFFREY M. SAMUELS

Attesting Officer     Acting Commissioner of Patents and Trademarks